(12) United States Patent
Shoher et al.

(10) Patent No.: US 6,213,776 B1
(45) Date of Patent: Apr. 10, 2001

(54) PRECIOUS METAL BONDING COMPOSITION

(76) Inventors: Itzhak Shoher, 50 Sholomo Hamelech St., Tel Aviv; Aharon Whiteman, 13 JL Peretz St., Petach Tikva, both of (IL)

( * ) Notice: Subject to any disclaimer, the term of this patent is extended or adjusted under 35 U.S.C. 154(b) by 0 days.

(21) Appl. No.: 09/535,800

(22) Filed: Mar. 28, 2000

(51) Int. Cl.⁷ ...................................................... A61C 13/08
(52) U.S. Cl. ............................................ 433/207; 433/226
(58) Field of Search ................................... 433/207, 208, 433/223, 226, 227, 228.1; 428/323, 328

(56) References Cited

U.S. PATENT DOCUMENTS 5,143,692 * 9/1992 Van Der Zel ............................ 419/8
5,332,622 * 7/1994 Shoher et al. ........................ 428/323
5,593,305 * 1/1997 Shoher et al. ........................ 433/218

* cited by examiner

Primary Examiner—John J. Wilson
Assistant Examiner—Melba Bumgarner

(57) ABSTRACT

A bonding material for joining a polymeric veneering material or porcelain ceramic to a metal framework of a dental restoration or dental prosthesis before sintering the porcelain at a suitable temperature to form a clinically unbreakable structure. The bonding material is composed of finely divided metal particles including at least 50% gold or a gold alloy as its major constituent and finely divided particles of a carbonaceous material preferably of activated carbon.

10 Claims, No Drawings

PRECIOUS METAL BONDING COMPOSITION

FIELD OF THE INVENTION

This invention relates to an improved precious metal bonding material composition for joining a polymeric veneering material or porcelain ceramic to a metal framework of a dental restoration or dental prosthesis.

BACKGROUND OF THE INVENTION

It is conventional in the field of restorative dentistry to cover the metal framework of a dental prosthesis or restorative restoration such as a crown or bridge with a polymeric veneering material such as acrylic or a porcelain ceramic to simulate the aesthetics of natural teeth. The veneering material forms the superstructure for the prosthesis or dental restoration after it is fused to the underlying metal framework at relatively high temperature. A superstructure of a porcelain ceramic composition may be formed of, for example, natural feldspar, quartz and kaolin and may possibly also include borosilicate glasses, flux and a coloring agent.

To enhance the bond strength between the metal framework and a porcelain superstructure it is conventional practice to apply a bonder to the surface of the metal framework upon which a porcelain ceramic material is coated before firing the porcelain ceramic at relatively high temperature in a dental furnace. A typical bonder contains a composition of finely divided particles of noble metals essentially or entirely of gold. An alternative bonding material which enhances the bond between a porcelain ceramic and a metal framework particularly of a noble metal or alloy composition is described in U.S. Pat. No. 4,434,211 the disclosure of which is herein incorporated by reference. In accordance with the aforementioned patent the bonder includes particles composed of a halide of a noble metal in a range of between 1 to 100% by weight of the bonder composition. Although a bonder having a halide of a noble metal results in a clinically unbreakable bond the success in forming a bond of satisfactory bond strength is nevertheless dependent upon firing the porcelain ceramic under controlled conditions in a relatively narrow temperature range.

SUMMARY OF THE INVENTION

A bonding material composed of a precious metal composition with gold as a major constituent has been discovered in accordance with the present invention which will form a clinically unbreakable bond between the metal framework of the dental restoration or prosthesis and a porcelain ceramic superstructure. Moreover, the porcelain can be sintered over a much wider temperature firing range than is presently possible and the bond strength is higher and more consistent over the entire sintering temperature firing range.

Broadly, the bonding material of the present invention comprises a composition of finely divided metal particles having at least 50% gold or gold alloy as the major metal constituent and finely divided particles of activated carbon in a range of from 0.05 wt % to 10 wt % of the weight of the composition. Finely divided metal particles other than gold may be included including non-precious metal particles and/or particles of a noble metal halide.

DETAILED DESCRIPTION OF THE INVENTION

The bonding material of the present invention should include at least 50 wt % gold or gold alloy and finely divided particles of a carbonaceous material of preferably activated carbon in a range of from 0.05 wt % to 10 wt % of the weight of the composition. Activated carbon is a well-known, porous, carbonaceous material formed by heat-treating carbon or subjecting it to reaction with gases, sometimes adding chemicals, for example, zinc chloride, during or after carbonization, in order to increase its porosity. Its high porosity results in a very high surface area of many orders of magnitude larger than its untreated surface area. The carbonaceous particles from which activated carbon is formed may be of any conventional carbon material, including carbon black, coke flour, calcined lamp black flour, and the like.

Although the activated carbon particles may be present in a range of from 0.05 wt % to 10 wt % of the total bonder composition a more preferred concentration range for activated carbon is between 0.1 wt % and 1.0 wt % of the total bonder composition. The size of the activated particles can vary between 0.5 and 250 microns but preferably at least 70% by weight of the activated carbon particles should have a size of between 5 and 150 microns. The presence of carbonaceous particles, preferably activated carbon, in the bonder composition within the above identified concentration range is essential to the present invention and acts as a solder binding itself to the the metal understructure. This provides for greater latitude in the formation of a clinically unbreakable bond independent of the porcelain ceramic composition and over a wider sintering temperature firing range.

The presence of gold as a major constituent of the binder composition is particularly important to bind a porcelain ceramic to a metal framework of a precious metal composition which contains gold or a gold alloy as a constituent thereof. However it should be understood that the framework may be of any suitable metal or metal alloy composition and is not limited to a metal framework of precious metal(s) or alloys thereof.

The bonder composition of the present invention may comprise, in addition to at least 50 wt % gold or gold alloy and activated carbon, finely divided particles of noble based metal(s) other than gold either in elemental form or as an alloy thereof, a halide of a noble metal and non-precious metal particles with the non-precious metal particles limited in concentration to no more than about 10 wt % of the total bonder composition. If a noble metal halide is included in the bonder composition it should preferably be selected from a halide of a noble metal of silver, platinum, palladium and gold such as, for example, silver chloride or platinum chloride.

The bonder composition of the present invention may be used with or without a suitable binder. If the bonder is suspended in a binder, the binder should be selected to permit the bonder to be easily and readily applied to the surface(s) of the metal framework by any conventional method, such as, brushing, painting, dipping and spraying before the porcelain ceramic material is applied and before the porcelain is sintered. Examples of a liquid binder include water detergents or an organic composition such as alcohol or ethylene glycol. Alternatively, a wax binder may also be used to cover or coat the metal surface(s) over which porcelain is to be applied. The binder selected should be one which will volatilize in the sintering process without leaving a residue. When a binder is not used the finely divided bonder particles may be sprinkled over the metal surface(s) upon which porcelain is to be applied before sintering. There is no coating thickness requirement for the bonder material.

After applying the bonding material of the present invention to the applicable surface(s) of the metal framework over which porcelain is to be applied the metal framework may be sintered at a temperature of between 800° C. and 1030° C. which is a temperature range considerably wider than the sintering temperature range heretofore necessary to produce an acceptable porcelain superstructure of adequate bond strength. The sintering operation causes the porcelain ceramic to fuse to the metal framework through the sintered bonding material which functions as a solder and mitigates for any differences in thermal contraction rates.

What is claimed:

1. A bonding material for joining a polymeric veneering material or porcelain ceramic to a metal framework of a dental restoration or prosthesis, said bonding material comprising a composition of finely divided metal particles having at least 50% gold or gold alloy as the major constituent thereof and finely divided particles of activated carbon, wherein the composition is disposed before sintering between the polymeric veneering material or porcelain ceramic and the metal framework.

2. A bonding material as defined in claim 1 wherein said activated carbon in a concentration range of from 0.05 wt % to 10 wt % of the weight of the composition.

3. A bonding material as defined in claim 2 wherein said particles of activated carbon is in a size range of from 0.5 and 250 microns.

4. A bonding material as defined in claim 3 wherein at least 70 wt % of said particles of activated carbon is in a size range of from 5 to 150 microns.

5. A bonding material as defined in claim 3 wherein said activated carbon is in a concentration range of from 0.1 wt % to 1.0 wt % of the weight of the composition.

6. A bonding material as defined in claim 3 wherein said bonding material further comprises finely divided metal particles of precious metal(s) other than gold in elemental form or as an alloy and up to about 10 wt % of non-precious metal particles.

7. A bonding material as defined in claim 6 wherein said bonding material further comprises finely divided metal particles of a noble metal halide.

8. A bonding material as defined in claim 3 wherein said bonding material further comprises finely divided metal particles of a noble metal halide.

9. A bonding material as defined in claim 8 wherein said noble metal halide is selected from the group of noble metals consisting of silver, platinum, palladium and gold.

10. A bonding material as defined in claim 3 further comprising a binder functioning as a carrier vehicle for the bonder material selected from the group consisting of water detergents, an organic composition and wax.

* * * * *